United States Patent
Bendjaballah

(12) 
(10) Patent No.: US 10,206,782 B1
(45) Date of Patent: Feb. 19, 2019

(54) CUSTOM-FITTING COLLAR SLEEVE BACKING FOR COMMERCIAL HIP PROTHESES

(71) Applicant: KING SAUD UNIVERSITY, Riyadh (SA)

(72) Inventor: Mohamed Zoubir Allaoua Bendjaballah, Riyadh (SA)

(73) Assignee: King Saud University, Riyadh (SA)

(*) Notice: Subject to any disclaimer, the term of this patent is extended or adjusted under 35 U.S.C. 154(b) by 39 days.

(21) Appl. No.: 15/782,493

(22) Filed: Oct. 12, 2017

(51) Int. Cl.
*A61F 2/32* (2006.01)
*A61F 2/30* (2006.01)
*A61F 2/36* (2006.01)

(52) U.S. Cl.
CPC ...... *A61F 2/30734* (2013.01); *A61F 2/30728* (2013.01); *A61F 2/30767* (2013.01); *A61F 2/3607* (2013.01); *A61F 2002/3038* (2013.01); *A61F 2002/3092* (2013.01); *A61F 2002/3093* (2013.01); *A61F 2002/30512* (2013.01); *A61F 2002/30729* (2013.01); *A61F 2002/30738* (2013.01); *A61F 2002/30934* (2013.01); *A61F 2002/365* (2013.01)

(58) Field of Classification Search
USPC .......... 623/20.14–20.2, 23.14–23.52
See application file for complete search history.

(56) References Cited

U.S. PATENT DOCUMENTS

| | | | |
|---|---|---|---|
| 5,047,061 A * | 9/1991 | Brown | A61B 17/8808 606/92 |
| 5,108,452 A | 4/1992 | Fallin | |
| 5,336,265 A | 8/1994 | Serbousek et al. | |
| 5,876,446 A * | 3/1999 | Agrawal | A61F 2/30767 606/76 |
| 6,336,941 B1 | 1/2002 | Subba Rao et al. | |
| 6,893,445 B1 * | 5/2005 | Revie | A61B 17/8808 606/86 R |
| 8,100,982 B2 | 1/2012 | Heck et al. | |
| 8,721,733 B2 | 5/2014 | Bonitati | |
| 2004/0015238 A1 * | 1/2004 | Buehler | A61B 17/8808 623/22.12 |
| 2006/0276906 A1 * | 12/2006 | Hoag | A61F 2/30767 623/23.34 |
| 2013/0261762 A1 * | 10/2013 | Kennedy | A61F 2/3609 623/22.42 |
| 2014/0188240 A1 | 7/2014 | Lang et al. | |

* cited by examiner

*Primary Examiner* — Yashita Sharma
(74) *Attorney, Agent, or Firm* — Richard C. Litman

(57) ABSTRACT

The custom-fitting collar sleeve backing for commercial hip prostheses includes a base and a top portion, the top portion being connected to the base. The base has a bottom surface defining an aperture. The aperture of the bottom surface is dimensioned and configured for receiving the neck portion of a hip prosthesis. The bottom surface of the base may have a beaded topology. The top portion includes a shoulder portion defining an aperture. The aperture of the shoulder portion includes an outwardly extending annular flange and is configured for fitting the cylindrical shaft of the neck portion of the hip prosthesis.

5 Claims, 3 Drawing Sheets

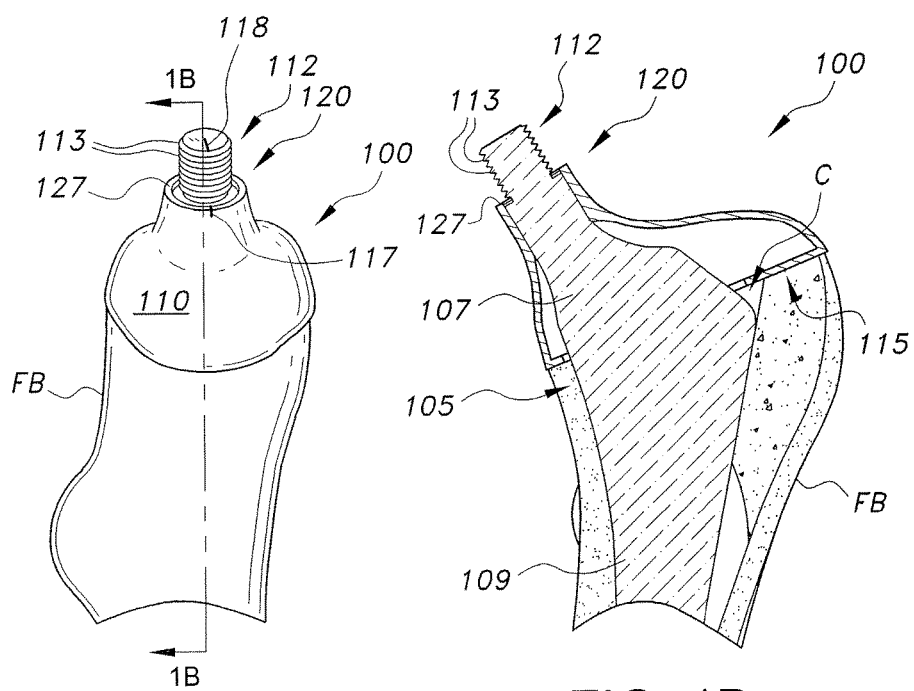
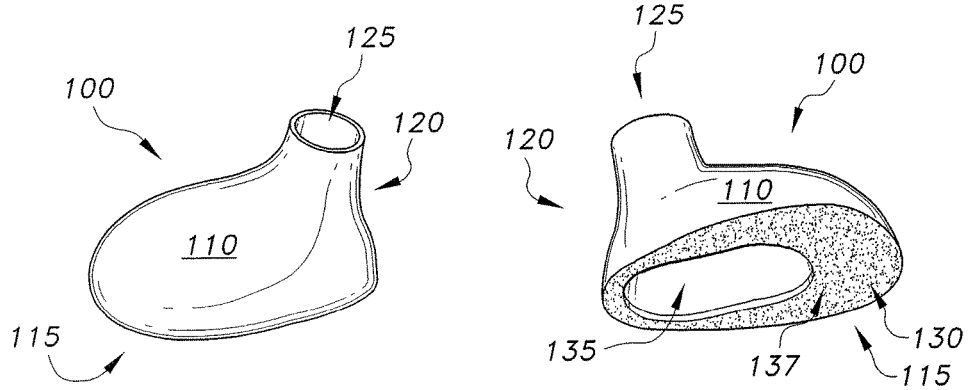
FIG. 1A
FIG. 1B
FIG. 2A
FIG. 2B

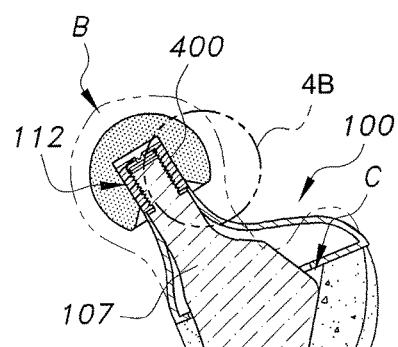
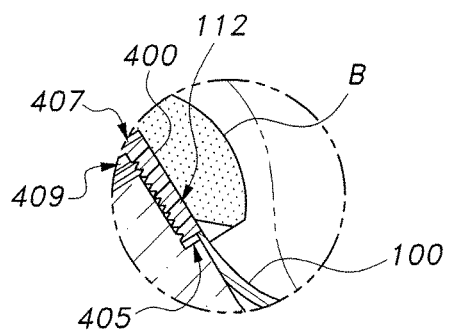
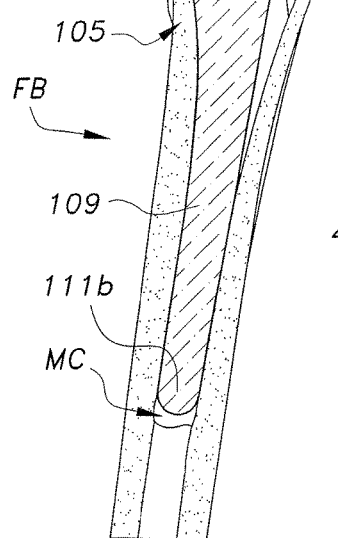
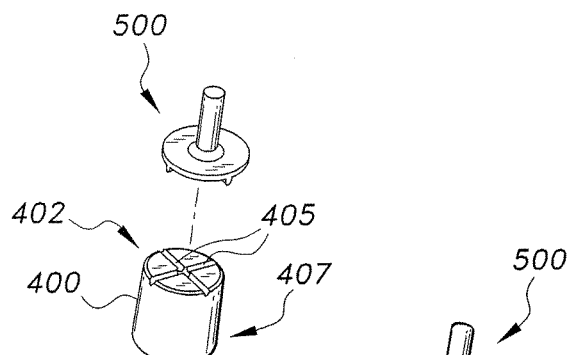
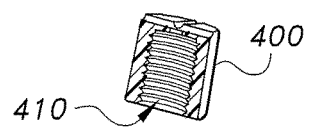
FIG. 4A
FIG. 4B
FIG. 5A
FIG. 5B
FIG. 5C

CUSTOM-FITTING COLLAR SLEEVE BACKING FOR COMMERCIAL HIP PROTHESES

BACKGROUND OF THE INVENTION

1. Field

The present disclosure relates to surgery and prosthetics, and particularly to providing a candidate for total hip replacement with a collar sleeve that custom fits his proximal femur, backing for the selected commercial hip prosthesis.

2. Description of the Related Art

Prosthetic implants for surgical repair of the hip joint are well known in the art. Typically, they are available as a two- or three-component system. The femoral stem typically extends into the medullary canal of the femoral shaft and is mounted with or without bone cement. One end of the femoral stem defines a neck that is typically attached to a ball that is positioned in communicating relation with the patient's acetabulum or a prosthetic acetabular cup fixed into the patient's acetabulum. A problem associated with such hip implants, however, is that the hip replacement drastically affects the load transfer within the proximal femur, leading to aseptic loosening and implant failure after a certain amount of time.

Thus, a custom-fitting collar sleeve backing for commercial hip prostheses solving the aforementioned problems is desired.

SUMMARY OF THE INVENTION

The custom-fitting collar sleeve backing for commercial hip prostheses includes a base and a top portion. The base includes a bottom surface having the shape of a sectioned bone with an aperture dimensioned and configured for receiving the neck portion of a hip prosthesis. The bottom surface of the base may have a beaded or porous topology to promote bone grafting to the base of the collar. The top portion includes a shoulder portion having an aperture dimensioned for fitting the top portion of the hip prosthesis' modified neck. A method of inserting the bone-fitting collar sleeve onto a prosthetic implant for hip prosthesis is also provided.

These and other features of the present disclosure will become readily apparent upon further review of the following specification and drawings.

BRIEF DESCRIPTION OF THE DRAWINGS

FIG. 1A is an environmental view of a custom-fitting collar sleeve backing for commercial hip prostheses, shown installed on a sectioned femoral bone.

FIG. 1B is a section view drawn along line 1B-1B of FIG. 1A.

FIG. 2A is a top perspective view of the collar sleeve of FIG. 1A.

FIG. 2B is a bottom perspective view of the collar sleeve of FIG. 1A.

FIG. 4A is an environmental side view in section of a femoral bone having a hip prosthesis implanted therein and the collar sleeve of FIG. 1A capping the prosthesis and femoral bone.

FIG. 4B is a detail view of area 4B of FIG. 4A.

FIG. 5A is an exploded perspective view of a torque meter chuck-mounted insert and a coupler nut used to secure the collar sleeve of FIG. 1A in position around the prosthesis and on top of the femoral bone.

FIG. 5B is a bottom perspective view of the torque meter chuck-mounted insert of FIG. 5A.

FIG. 5C is a perspective view in section of the coupler nut of FIG. 5A.

Similar reference characters denote corresponding features consistently throughout the attached drawings.

DETAILED DESCRIPTION OF THE PREFERRED EMBODIMENTS

Figures 3A, 3B:
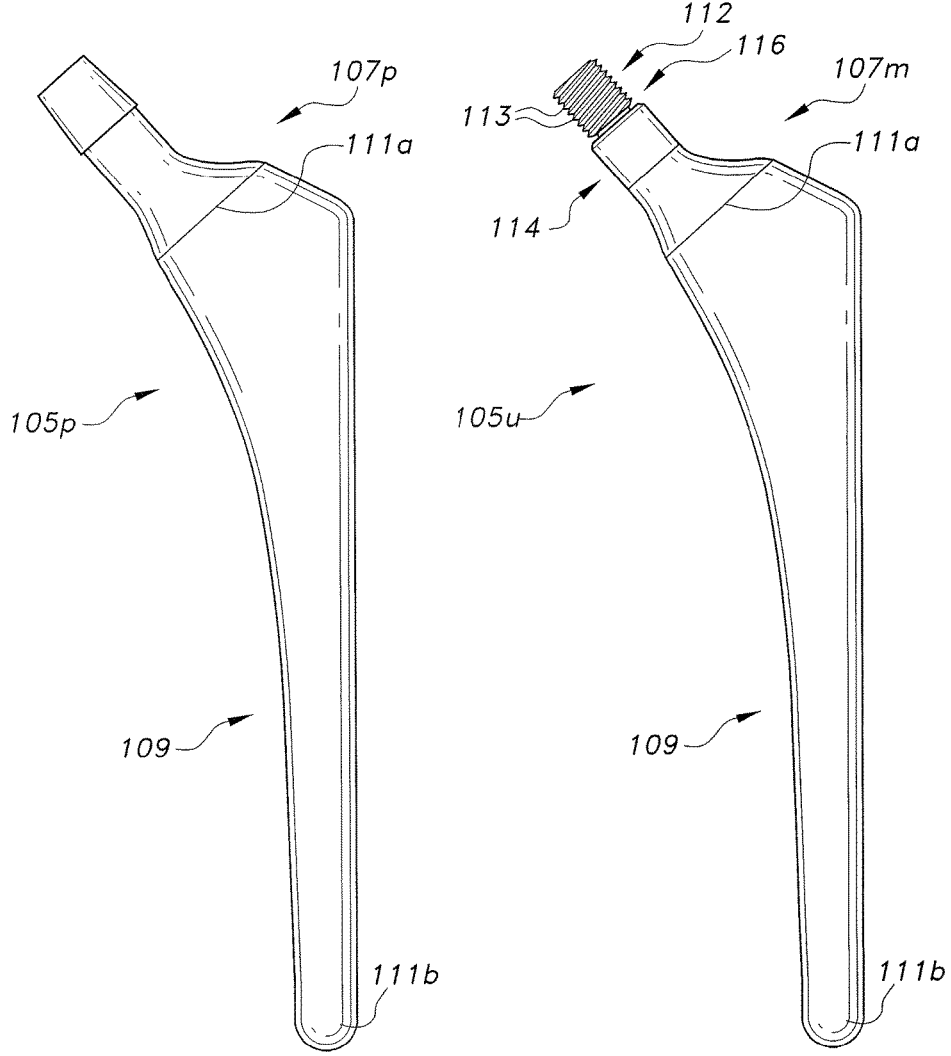
FIG. 3A is a right side view of a sample hip prosthesis of the prior art, which has been selected for implant surgery.
FIG. 3B is a right side view of a hip prosthesis of FIG. 3A, shown after modification of the neck portion to accommodate the collar sleeve of FIGS. 2A and 2B.

Referring to FIGS. 2A and 2B, the custom-fitting collar sleeve backing for commercial hip prostheses is a collar sleeve 100 that is custom designed and configured for interfacing a modified hip prosthesis 105 with a patient's proximal femur. As shown in FIG. 3A, the hip prosthesis 105p generally includes a femoral stem 109 having a proximal end 111a and an opposing distal end 111b, as well as a neck portion 107p protruding outward from the proximal end 111a of the femoral stem 109. The distal end 111b of the femoral stem 109 is adapted for insertion into a canal C reamed within the medullary cavity MC of a femoral bone FB, as shown in FIG. 4A.

As shown in FIGS. 3A and 3B, the neck portion 107p of the original hip prosthesis 105p is modified to receive the collar sleeve 100, the modified hip prosthesis being generally referred to as 105u and the modified neck portion being generally referred to as 107m. The modified neck portion 107m includes a threaded tip 112, a cylindrical shaft 114, and an annular groove 116 between the threaded tip 112 and the cylindrical shaft 114. The threaded tip 112 has external threads 113 and a prosthesis alignment indicator 118 (shown in FIG. 1A). As shown in FIGS. 4A-4B, a prosthetic ball B is set on a tapered coupling nut 400 screwed onto the implant's threaded tip 112 so that the ball B may be positioned accurately in relation with the acetabular component of the hip prosthesis 105u.

The collar sleeve 100 includes a base 115 and a top portion 110, the top portion 110 being connected to the base 115. The base 115 includes a bottom surface 130 having an aperture 135 defined therein. The aperture 135 is dimensioned and configured for receiving the modified neck portion 107m of the of the modified hip prosthesis 105u. The top portion 110 is dimensioned and configured for covering the modified neck portion 107m of the modified hip prosthesis 105u and includes a shoulder portion 120 defining an aperture 125. The aperture 125 of the shoulder portion 120 is dimensioned and configured for receiving the modified neck portion 107m of the modified hip prosthesis 105u and fits with the cylindrical shaft 114 of the modified neck portion 107m of the modified hip prosthesis 105u, as shown in FIGS. 1A and 1B. The body of the collar sleeve 100 has a thin skin made of a biocompatible material, either empty or enclosing a porous cellular lattice structure exposed on the bottom surface so that the proximal end of the femur can grow into the cellular structure, grafting the sleeve 100 onto the bone.

Further, the aperture 125 of the shoulder portion 120 includes an outwardly extending annular flange 127. The collar sleeve 100 is made to rest on top of the sectioned bone and properly secured in place by aligning the collar alignment indicator 117 to the prosthesis alignment indicator 118.

The thin outer skin of the sleeve 100 should conform to the patient's epiphyseal femoral anatomy. The bottom surface 130 of the base 115 of the collar sleeve 100 may have a beaded topology 137, the gaps in the beaded topology 137 matching the approximate size of the pores in the femoral bone FB in order to stimulate the growth of cells within the gaps in the beaded topology 137; thereby securing the collar sleeve 100 to the femoral bone FB. Alternatively, the bottom surface 130 of the base 115 may be perforated or etched to boost the cell growth process.

The coupler nut 400 (shown in FIGS. 4A and 5A) is threaded onto the threaded tip 112 of the hip prosthesis 105u to secure the collar sleeve 100 onto the femoral bone FB once the collar sleeve 100 has been properly positioned on the modified neck portion 107m of the modified hip prosthesis 105u. The nut 400 includes a top face 402 having a plurality of tightening slots 405 (preferably two tightening slots), internal threads 410, and an outer surface 407 having a Morse taper for a friction fit with a complementary taper of the internal bore of the prosthetic ball B. The coupler nut 400 fastens the sleeve 100 to the modified hip prosthesis 105u, thereby clamping the collar sleeve 100 against the femoral bone.

The nut 400 may be tightened via the use of a torquemeter chuck-mounted insert (or adapter) 500 to achieve a secure contact between the bottom surface 130 of the base 115 of the collar sleeve 100 and the femoral bone FB without pulling out the prosthetic implant 105 from the canal C created within the medullary cavity MC of the femoral bone FB. For example, the torque-meter chuck-mounted insert 500 can be inserted onto the face 402 of the nut 400, such that cruciform projections on the face of the insert 500 may fit into the tightening slots 405 on the top face of the coupler nut 400, as shown in FIG. 5A, to tighten the nut 400 onto the threaded tip 112 of the neck portion 107. Once the nut 400 is positioned, between the ball B and the modified neck portion 107m of the modified hip prosthesis 105u, the nut 400 may transmit the compressive force jointly to the prosthetic implant 105 and the collar sleeve 100 via the threads 113 and the shoulder portion 120, respectively, while bending movements may be translated to the modified hip prosthesis 105u and then to the collar sleeve 100 via the modified neck portion 107m of the modified hip prosthesis 105u, provided that suitable clearances 405, 407, and 409 are assured.

By way of operation, prior to implanting the modified hip prosthesis 105u in the femoral bone FB, a medical professional, such as an orthopedic surgeon, has to first resect (i.e., remove) the femoral head (i.e., illustrated by the silhouette line in FIGS. 4A and 4B) from the femoral bone FB, so that the canal C may be created within the femoral shaft FA by excavating cortical and cancellous bone tissue from the femoral shaft FS of the femoral bone FB and preparing the femoral shaft FS of the femoral bone FB to receive the femoral stem 109 of the modified hip prosthesis 105u. Prior to inserting the femoral stem 109 of the modified hip prosthesis 105u into the canal C, however, the original neck portion 107p of the original hip prosthesis 105p must first be modified to include the threaded tip 112, the cylindrical shaft 114, and the annular groove 116, as illustrated in FIG. 3B. Once the original neck portion 107p has been properly modified, the femoral stem, generally referred to as 109, may be inserted into the canal C and secured within the canal C with or without bone cement.

The modified neck portion 107m of the modified hip prosthesis 105u is then inserted into the aperture 135 of the bottom surface 130 of the collar sleeve 100, such that the threaded tip 112 may extend through the aperture 125 of the shoulder portion 120 of the collar sleeve 100 and the annular flange 127 may be positioned around the cylindrical shaft 114 of the modified neck portion 107m, thereby positioning the bottom surface 135 of the base 115 in communicating relation with the femoral bone FB, as shown in FIGS. 1A and 1B. Once the collar sleeve 100 is mounted on the modified neck portion 107m of the modified hip prosthesis 105u, the collar sleeve 100 is tuned in place to align each of the alignment indicators 117, 118 to ensure that the collar sleeve 100 is properly positioned on the modified neck portion 107m of the modified hip prosthesis 105u. Since the collar sleeve 100 is designed in context with the sectioned bone and the modified implant, both collar-implant and collar-bone interactions are simultaneously and properly assured.

The coupler nut 400 is then threaded onto the threaded tip 112 of the modified neck portion 107m to secure the collar sleeve 100 in place. The torque-meter chuck-mounted insert 500 may then be inserted onto the face 402 of the nut 400, such that the insert 500 may fit into the tightening slots 405, as shown in FIG. 5A, to tighten the nut 400 onto the threaded tip 112 of the modified neck portion 107m without pulling the hip prosthesis 105 out of the canal C created within the medullary cavity MC of the femoral bone FB.

It is to be understood that the present invention is not limited to the embodiments described above, but encompasses any and all embodiments within the scope of the following claims.

I claim:

1. A custom-fitting collar sleeve backing for commercial hip prostheses, the collar sleeve comprising a body having:
    a base having a bottom surface, the bottom surface having a lower aperture defined therein, the lower aperture in the bottom surface being dimensioned and configured for receiving a modified neck portion of a modified hip prosthesis;
    a top portion extending from the base, the top portion having an enclosed, cylindrical shoulder portion having an upper aperture defined therein, the upper aperture of the shoulder portion having an outwardly and upwardly extending annular flange, the upper aperture being dimensioned and configured for fitting a corresponding cylindrical shape of the neck portion of the hip prosthesis;
    the body having a thin skin of biocompatible material and the bottom surface having a porous cover, whereby the sleeve is adapted to be grafted onto a patient's femoral bone by growth of bone tissue; and
    a coupler nut having internal threads and an external Morse taper, the coupler nut being adapted for fastening onto a threaded tip of a hip prosthesis and bearing against the top portion of the sleeve in order to secure the collar sleeve onto the hip prosthesis and in contact with the sectioned bone, the coupler nut being adapted for tapered friction fit of a prosthetic ball thereto replacing a head of the patient's femoral bone,
    wherein interactions between the prosthetic ball, coupler nut, and collar sleeve will help restore load transfer on the bone to approximate pre-surgical load transfer.

2. The custom-fitting collar sleeve according to claim 1, wherein the shoulder portion further comprises a collar alignment indicator.

3. The custom-fitting collar sleeve according to claim 1, wherein the porous cover on the bottom surface of the base is beaded.

4. A method for inserting a collar sleeve onto a modified hip prosthesis, comprising the steps of:
 providing a hip prosthesis, the hip prosthesis including a femoral stem having a proximal end and an opposing distal end, and a neck portion extending from the proximal end of the femoral stem;
 modifying the neck portion of the hip prosthesis to include a threaded tip, a cylindrical shaft, and an annular groove between the threaded tip and the cylindrical shaft;
 providing a collar sleeve, the collar sleeve comprising a body having:
  a base having a bottom surface, the bottom surface having a lower aperture defined therein, the lower aperture in the bottom surface being dimensioned and configured for receiving a modified neck portion of a modified hip prosthesis; and
  a top portion extending from the base, the top portion having an enclosed shoulder portion having an upper aperture defined therein, the upper aperture of the shoulder portion having an outwardly and upwardly extending annular flange, the upper aperture being dimensioned and configured for fitting the cylindrical shape of the neck portion of the hip prosthesis therethrough;
  the body having a thin skin of biocompatible material and the bottom surface having a porous cover, whereby the sleeve may be grafted onto a patient's femoral bone by growth of bone tissue; and
 a coupler nut having internal threads and an external Morse taper, the coupler nut being adapted for fastening onto the threaded tip of a hip prosthesis and bearing against the top portion of the sleeve in order to secure the collar sleeve onto the hip prosthesis and in contact with the sectioned bone, the coupler nut being adapted for tapered friction fit of a prosthetic ball thereto replacing a head of the patient's femoral bone,
 inserting the neck portion of the hip prosthesis into the lower aperture of the bottom surface of the base of the collar sleeve;
 inserting the threaded tip and the cylindrical shaft of the neck portion through the upper aperture of the shoulder portion of the collar sleeve; and
 threading a coupler nut onto the threaded tip of the neck portion of the hip prosthesis until the coupler nut rests against the top surface of the collar sleeve shoulder.

5. The method for inserting a collar sleeve onto a hip prosthesis according to claim 4, further comprising the step of tightening the coupler nut with a chuck-mounted torquemeter insert.

* * * * *